US012575752B2

(12) United States Patent
Akduman et al.

(10) Patent No.: US 12,575,752 B2
(45) Date of Patent: Mar. 17, 2026

(54) MICROWAVE BREAST CANCER SCREENING SYSTEM

(71) Applicant: ISTANBUL TEKNIK UNIVERSITESI, Istanbul (TR)

(72) Inventors: Ibrahim Akduman, Istanbul (TR); Tuba Yilmaz Abdolsaheb, Istanbul (TR); Aleksandar Janjic, Istanbul (TR)

(73) Assignee: ISTANBUL TEKNIK UNIVERSITESI, Istanbul (TR)

( * ) Notice: Subject to any disclaimer, the term of this patent is extended or adjusted under 35 U.S.C. 154(b) by 2 days.

(21) Appl. No.: 18/294,606

(22) PCT Filed: May 24, 2022

(86) PCT No.: PCT/TR2022/050474
§ 371 (c)(1),
(2) Date: Feb. 2, 2024

(87) PCT Pub. No.: WO2023/014320
PCT Pub. Date: Feb. 9, 2023

(65) Prior Publication Data
US 2025/0114006 A1 Apr. 10, 2025

(30) Foreign Application Priority Data
Aug. 2, 2021 (TR) ................................ 2021/012195

(51) Int. Cl.
*A61B 5/0507* (2021.01)
*A61B 5/00* (2006.01)

(52) U.S. Cl.
CPC .......... *A61B 5/0507* (2013.01); *A61B 5/4312* (2013.01)

(58) Field of Classification Search
CPC ....... A61B 5/0507; A61B 5/05; A61B 5/4312; A61B 10/0041; A61B 5/708; A61B 6/502
See application file for complete search history.

(56) References Cited

U.S. PATENT DOCUMENTS 4,774,961 A * 10/1988 Carr ..................... A61B 5/4312
374/E11.003
6,421,550 B1* 7/2002 Bridges .................. G01N 22/00
600/407

(Continued)

FOREIGN PATENT DOCUMENTS

CA        1291220 C    10/1991
EP        0222315 A2    5/1987
(Continued)

OTHER PUBLICATIONS

W. C. Chew, Waves and Fields in Inhomogenous Media, IEEE Press New York, 1995.

(Continued)

*Primary Examiner* — Oommen Jacob
(74) *Attorney, Agent, or Firm* — Bayramoglu Law Offices LLC

(57) ABSTRACT

A microwave-based breast cancer screening and early diagnostics imaging system is provided. The microwave-based breast cancer screening and early diagnostics imaging system uses mild compression to electromagnetically homogenize the heterogeneous breast media or, to some degree, decrease the breast dimension to 2D. The device is capable of providing multi-angle examination, if necessary, and produces horizontal and vertical cross-sectional images based on the polarization of the antennas used for scanning. Merging two-sectional images can give a possibility of 3D microwave representation of the breast tissue that allows identification of the malignant/cancerous/harmful tissues/cells through cross validation.

2 Claims, 16 Drawing Sheets

(56) References Cited

U.S. PATENT DOCUMENTS

| | | | | |
|---|---|---|---|---|
| 9,029,778 | B1 * | 5/2015 | Boyd | G01S 13/89 |
| | | | | 250/341.1 |
| 10,258,251 | B2 * | 4/2019 | Canli | A61B 5/0536 |
| 11,510,728 | B2 * | 11/2022 | Bannister | A61B 34/20 |
| 2002/0193849 | A1 * | 12/2002 | Fenn | A61N 5/02 |
| | | | | 607/101 |
| 2004/0092826 | A1 * | 5/2004 | Corbeil | A61B 6/0435 |
| | | | | 600/476 |
| 2006/0241409 | A1 * | 10/2006 | Winters | A61B 5/05 |
| | | | | 600/430 |
| 2010/0067770 | A1 * | 3/2010 | Persson | A61B 5/0507 |
| | | | | 382/132 |
| 2014/0303701 | A1 * | 10/2014 | McKenna | A61N 2/004 |
| | | | | 607/113 |
| 2014/0309522 | A1 * | 10/2014 | Fullerton | A61B 90/39 |
| | | | | 600/424 |
| 2015/0371380 | A1 * | 12/2015 | Meaney | A61B 5/4312 |
| | | | | 382/131 |
| 2016/0106334 | A1 * | 4/2016 | Canli | A61B 5/7264 |
| | | | | 600/425 |
| 2017/0188874 | A1 * | 7/2017 | Suhami | A61B 5/0042 |
| 2021/0137406 | A1 * | 5/2021 | Lepple-Wienhues | |
| | | | | A61B 5/0507 |

FOREIGN PATENT DOCUMENTS

| | | |
|---|---|---|
| EP | 2063776 A1 | 6/2009 |
| WO | 2009146881 A2 | 12/2009 |

OTHER PUBLICATIONS

Loreto Di Donato, et al., Inverse Scattering Via Virtual Experiments and Contrast Source Regularization, IEEE Transactions on Antennas and Propagation, 2015, pp. 1661677, vol. 63 No. 4.

David Colton, et al., Inverse Acoustic and Electromagnetic Scattering Theory, 1992, Springer, Third Edition.

Tomasz M. Grzegorczyk, et al., Fast 3-D Tomographic Microwave Imaging for Breast Cancer Detection, IEEE Transactions On Medical Imaging, 2012, pp. 1584-1592, vol. 31 No. 8.

* cited by examiner

MICROWAVE BREAST CANCER SCREENING SYSTEM

CROSS REFERENCE TO THE RELATED APPLICATIONS

This application is the national phase entry of International Application No. PCT/TR2022/050474, filed on May 24, 2022, which is based upon and claims priority to TR2021/012195, filed on Aug. 2, 2021, in the Republic of Turkey, the entire contents of which are incorporated herein by reference.

TECHNICAL FIELD

The invention relates to a microwave-based breast cancer screening and early diagnostics imaging system which uses mild compression to, some extent, electromagnetically homogenize the heterogeneous breast media or to, some degree, decrease the breast dimension to 2D. The device is capable of providing multi-angle examination, if necessary, and produces horizontal and vertical cross-sectional images based on the polarization of the antennas used for scanning. Merging two-sectional images can give a possibility of 3D microwave representation of the breast tissue that allows identification of the malignant/cancerous/harmful tissues/cells through cross validation.

BACKGROUND

Currently, mammography is considered as a 'gold' standard for breast cancer imaging and it is usually utilized for women over 40 years of age. In addition to mammography, ultrasonography or magnetic resonance imaging is used if the patient is of a younger age, or is considered as a high-risk individual. If a suspicious lesion is noticed, the patient is referred to biopsy.

Mammography uses X-rays, a type of ionized radiation, thus is not performed on the women under the age of 40 and each patient is recommended to receive periodical examination with usually once a year repetition. This procedure periodically exposes the patient to X-rays. Additionally, mammography is limited by several known risks such as overdiagnosis, false-positive results and patient discomfort during the examination. Mammography yields high performance rate in fatty breasts (the breasts characterized by containing low levels of fibroglandular tissues) contrary to the accuracy rate of as low as 30% reported for the dense breasts (higher content of fibroglandular tissue). After the detection of suspected lesion, radiologist decides if further examinations, such as biopsy, is going to be performed.

Ultrasonography is mostly used as a supplementary technique to mammography. It can also be used as a part of regular breast check-ups performed for the younger women population (women under the age of 40). Use of ultrasonography can aid in detecting early stage mammographically occult lesions inside dense breasts, while carrying substantial risk of producing false positive results. As ultrasonography cannot distinguish between malignant and benign lesions, it offers a rather low selectivity rate. As in the case of mammography, based on the results, the physician determines if the diagnosis will be followed with a biopsy. Magnetic resonance imaging is mostly used in the high-risk patient groups and is limited by scanning time and scan per patient/device costs making it unsuitable for early cancer detection. Considering the limitations of currently used methodologies, there is a need for alternative imaging approaches that can potentially aid the field of breast cancer early screening and diagnostics. To this end, microwave imaging is emerging as a promising candidate technique that potentially provide a novel approach to breast cancer imaging.

Microwave breast cancer imaging, having clinical trials already conducted up to this point, gained momentum in the past 20 years. In this context, multi-static and bi-static cylindrical and spherical screening configurations were proposed. Antenna polarizations in bi-static spherical screening systems vary based on the orientation of spherical antenna carriers and therefore, such systems cannot provide high accuracy imaging. On the other hand, multi-static spherical screening systems are designed in line with radar operation principles. However, the main problem experienced in such systems is the misdiagnoses due to mismatch between the focal point of the field and the position of the malignant/cancerous tissues.

Cylindrical screening systems, when compared to spherical ones, deliver a superior performance when the microwave imaging approaches which consider inverse scattering problem are implemented. Rapid attenuation of the electromagnetic field, due to the losses induced by the breast tissues (high loss mediums), and the inability of highly accurate measurements of scattering parameters related to tissue heterogeneity complicate the detection process, and consequently the diagnosis of the malignant/cancerous tissues.

The system described in the International patent document with WO2009146881 number, available in the state of the art discloses a cone-shaped holder and antennae surrounding the holder. Moreover, the holder comprises a system that functions as a vacuum and it is aimed to prevent air gaps from forming between the breast tissue and the walls of the cone-shaped holder. The described system proposes a device that utilizes radar-based microwave imaging approach. The proposed system is able to radiate to the breast tissue from various angles through the angular movement of bi-static antennae. Accordingly, the system disclosed in said patent document differs from the planar screening system proposed in the present invention in that it performs radar-based and bi-static screening.

The patent document with EP2063776 number, available in the state of the art discloses a Magnetic Resonance (MR) imaging system. It is well known that the MR systems particularly underperform when imaging soft tissues and therefore, contrast agents are usually used to enhance the obtained images. Accordingly, said patent document discloses nuclear magnetic resonance (NMR) that depends on contrast agent enhanced imaging basis. The working principle of NMR is based on the detection of, through coils, the magnetic field emitted by protons excited via magnetic signals. Accordingly, in the proposed system, the transmitting magnet, shown in in FIG. $1a$ (1) in the said patent, illustrates the tissue and the emitted signals are picked up by the receiving coils. Again, the segmented structure illustrated in FIGS. $3a$-$3e$ in said patent document is used for stabilizing the breast tissue. To this end, the proposed system is used for stabilizing the breast tissue rather than compressing it. Furthermore, the described system in the said patent differs from the system proposed with the present invention in that it uses MR.

The Canadian patent document with CA1291220 number, available in the state of the art discloses a microwave system developed for locating breast tumours and for screening the breast tissue. It is assumed in the said patent that the temperature of malign tumour tissues differs from the temperature of a healthy tissue, and therefore, techniques such as infrared thermography are used for the diagnosis of a malignant tumour tissue. The said patent proposes to exploit the inherent temperature discrepancy between the malignant tumour and healthy tissue with microwave radiometry to detect the presence of a malignant tumour. However, it should be noted that the microwave radiometry-based systems have prolonged screening time (up to 30 minutes), due to the utilization of a single antenna. Also, such systems may yield false negative results, namely type 2 errors in tumours located at the deep tissues. Therefore, in order the resolve these two drawbacks the said document proposed to utilize antenna arrays instead of a single antenna in microwave radiometry systems and reduce the thickness of the breast tissue through tissue compression for deep tissue tumour detection. However, detailed designs and examples that can perform such operations are not given.

An examination on the systems available in the state of the art necessitates the development of the proposed invention in this work which comprises a planar breast cancer screening system that allows application of a mild compression to the heterogeneous breast tissue in order to, some extent, electromagnetically homogenize or render the tissue to, some extent, two dimensions. The system further allows to acquire images from different cross-sections of the breast tissue by radiating it with antenna arrays of different polarizations (e.g., horizontally and vertically polarized) from different angles. Finally, through cross-validation of the collected cross-sectional images cancerous/malignant/harmful tissue/cells can be identified.

SUMMARY

The object of the present invention is to provide a breast cancer screening system. The system enables the detection of cancerous/malignant/harmful tissues/cells using harmless, non-ionized electromagnetic waves in order to penetrate the breast tissue.

Another object of the present invention is to provide a breast cancer screening system that allows mild breast compression which to, some extent, electromagnetically homogenizes the heterogeneous breast structure which allows to reconstruct better accuracy microwave images.

Yet another object of the present invention is to provide a breast cancer screening system that eliminates problems associated with the wave attenuation induced by the breast tissue heterogeneity and lossy nature of the tissue.

Yet another object of the present invention is to provide a multi-angle breast screening that allows to acquire multiple 2D horizontal and vertical sectional data by radiating the breast from different angle positions.

Yet another object of the present invention is to provide 3D representation of the breast tissue by the means of combining 2D sectional images collected from different angles as well as horizontal and vertical polarizations.

Yet another object of the present invention is to provide an axial and coronal representation of the breast with the screening system that enables both vertical and horizontal sectional imaging through the dual antenna arrays polarizations (e.g., horizontally and vertically polarized arrays). This approach enables comparison of a suspected lesion through cross-validation.

BRIEF DESCRIPTION OF THE DRAWINGS

The system provided to achieve the objects of the present invention is illustrated in the figures attached.

In Said Figures.

Figure 1:
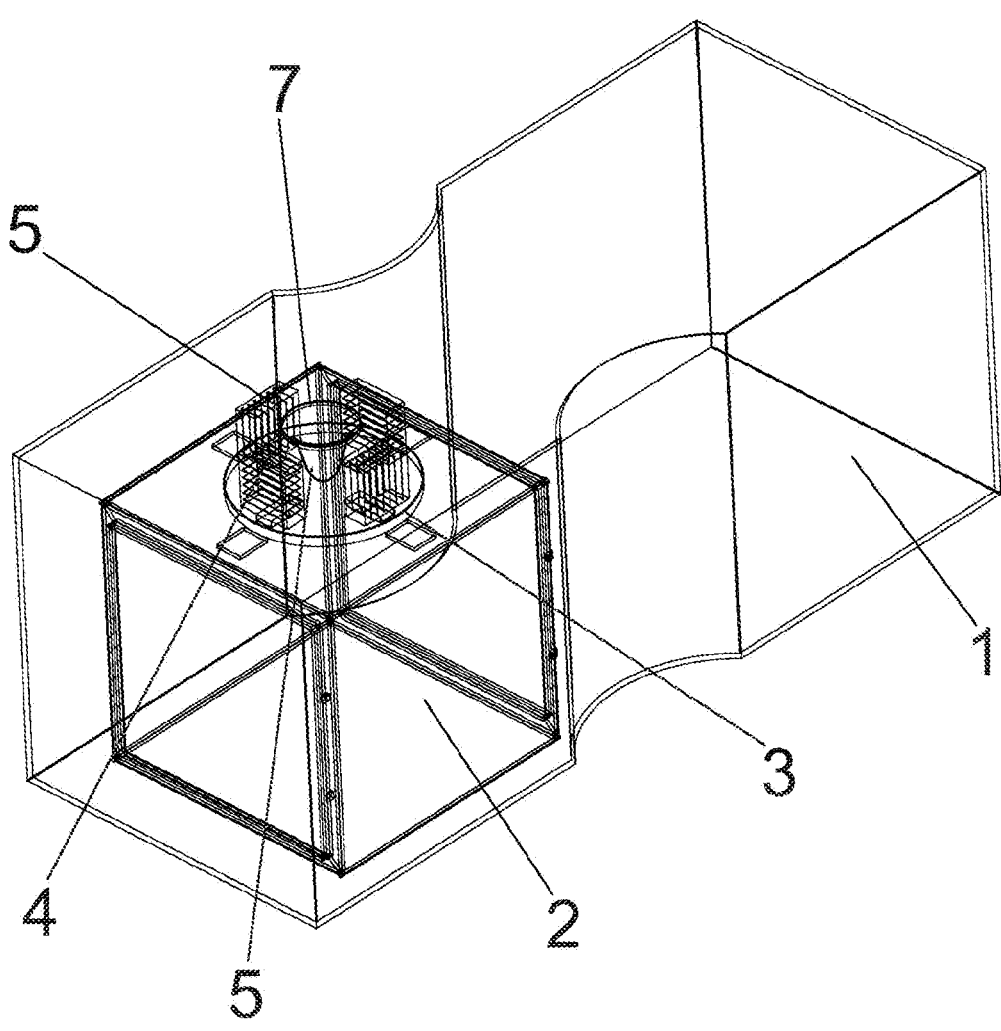
FIG. 1 illustrates the perspective view of the breast cancer screening system invention.
Figure 2:
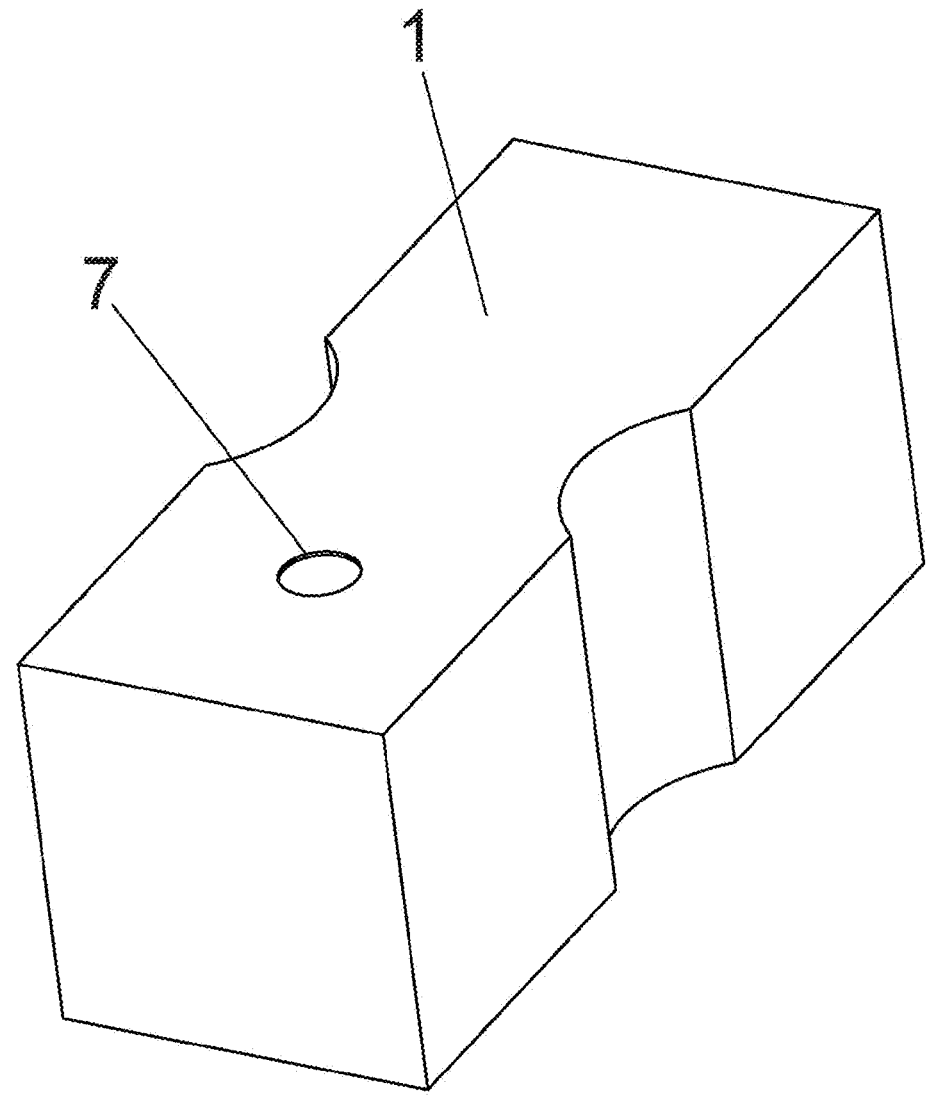
FIG. 2 illustrates the view of the bed compartment included in the breast cancer screening system invention.
Figure 3:
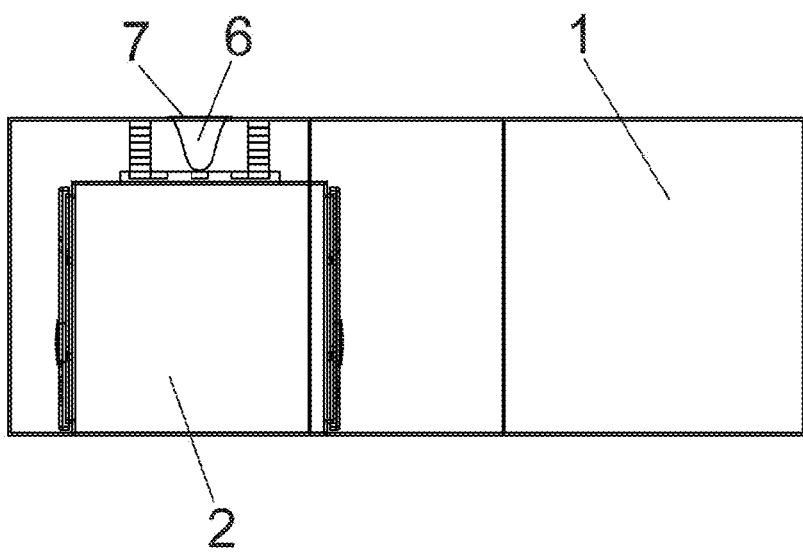
FIG. 3 illustrates the side view of the breast cancer screening system invention.
Figure 4:
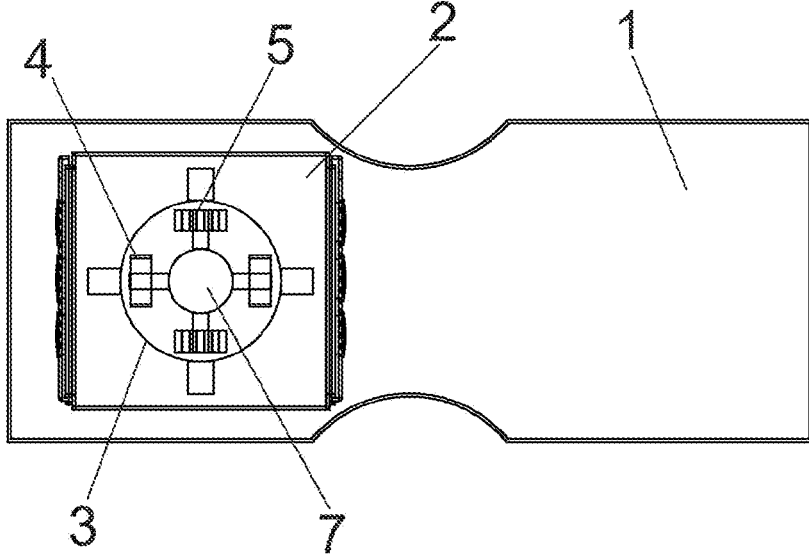
FIG. 4 illustrates the top view of the breast cancer screening system invention.
Figure 5:
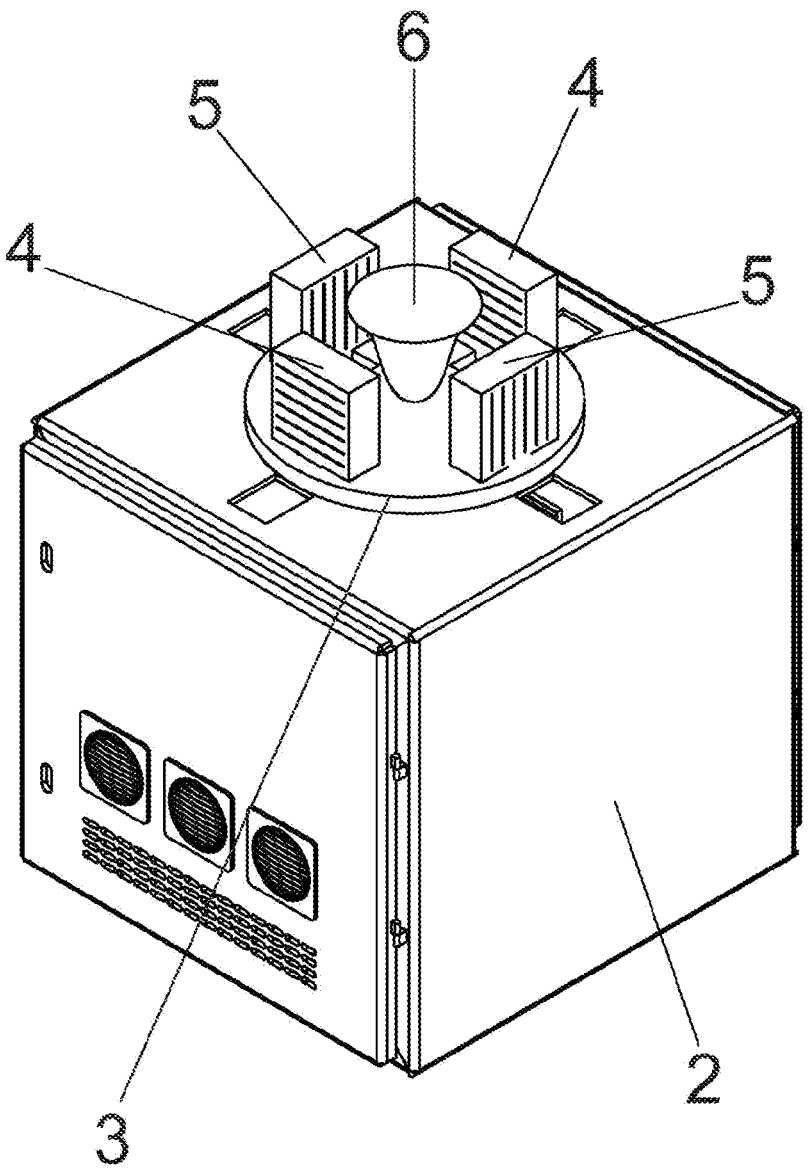
FIG. 5 illustrates the main measurement unit in an empty state of the breast cancer screening system invention.
Figure 6:
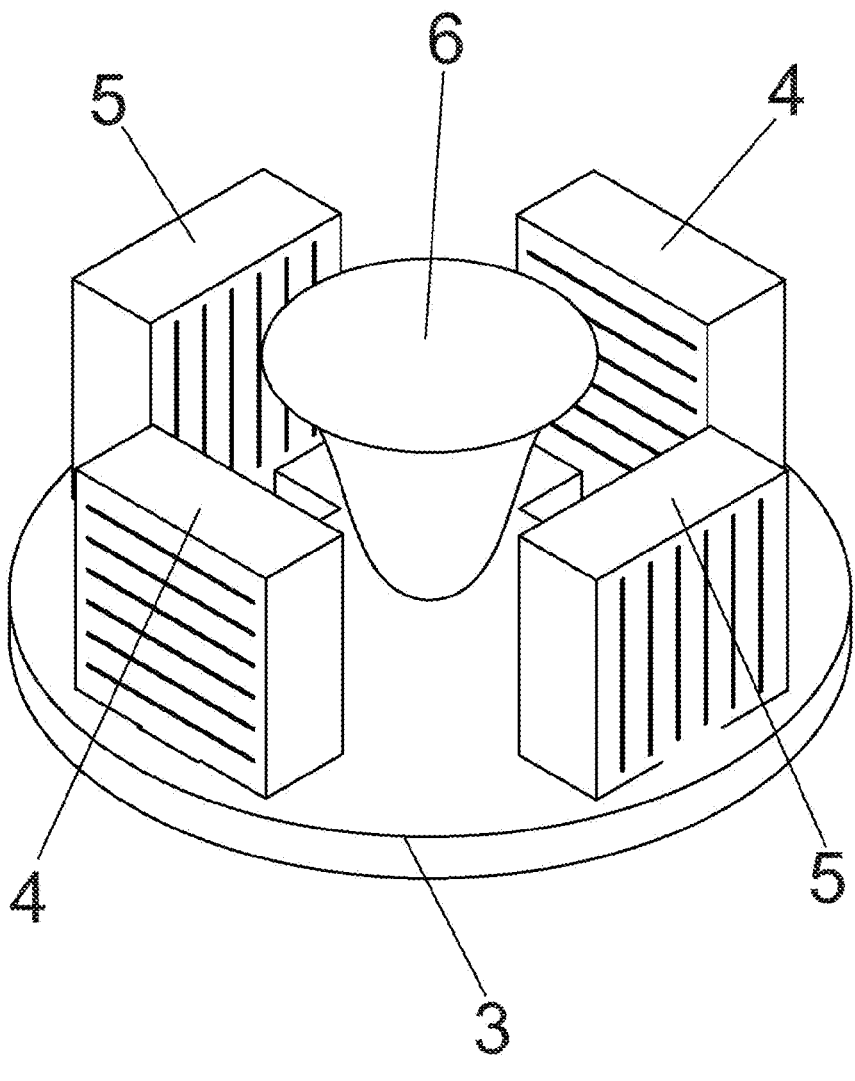
FIG. 6 illustrates the antenna blocks of the system in an empty state of the invention.
Figure 7:
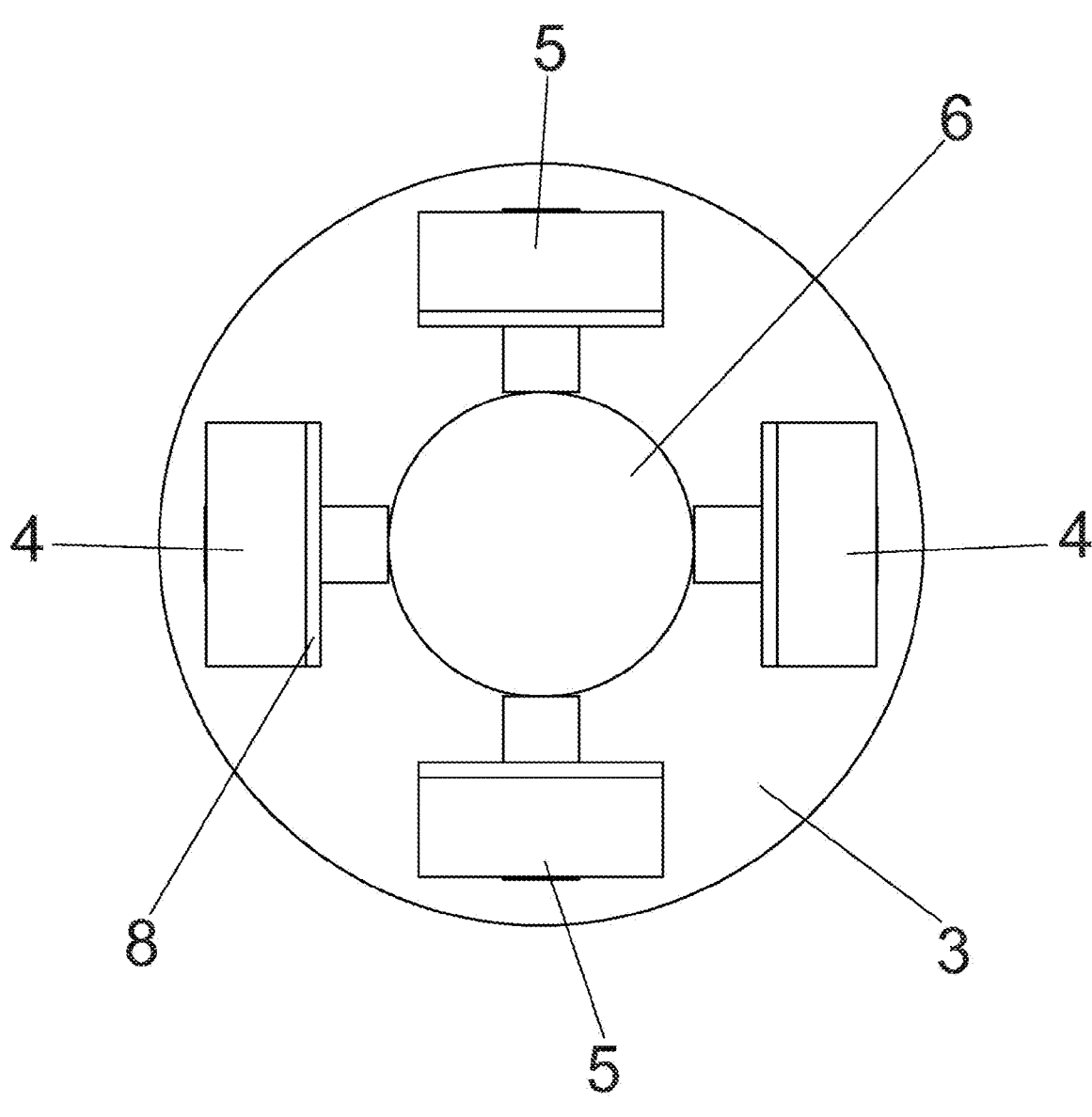
FIG. 7 illustrates the top view of the antenna blocks with a matching media included in the screening system invention.
Figure 8:
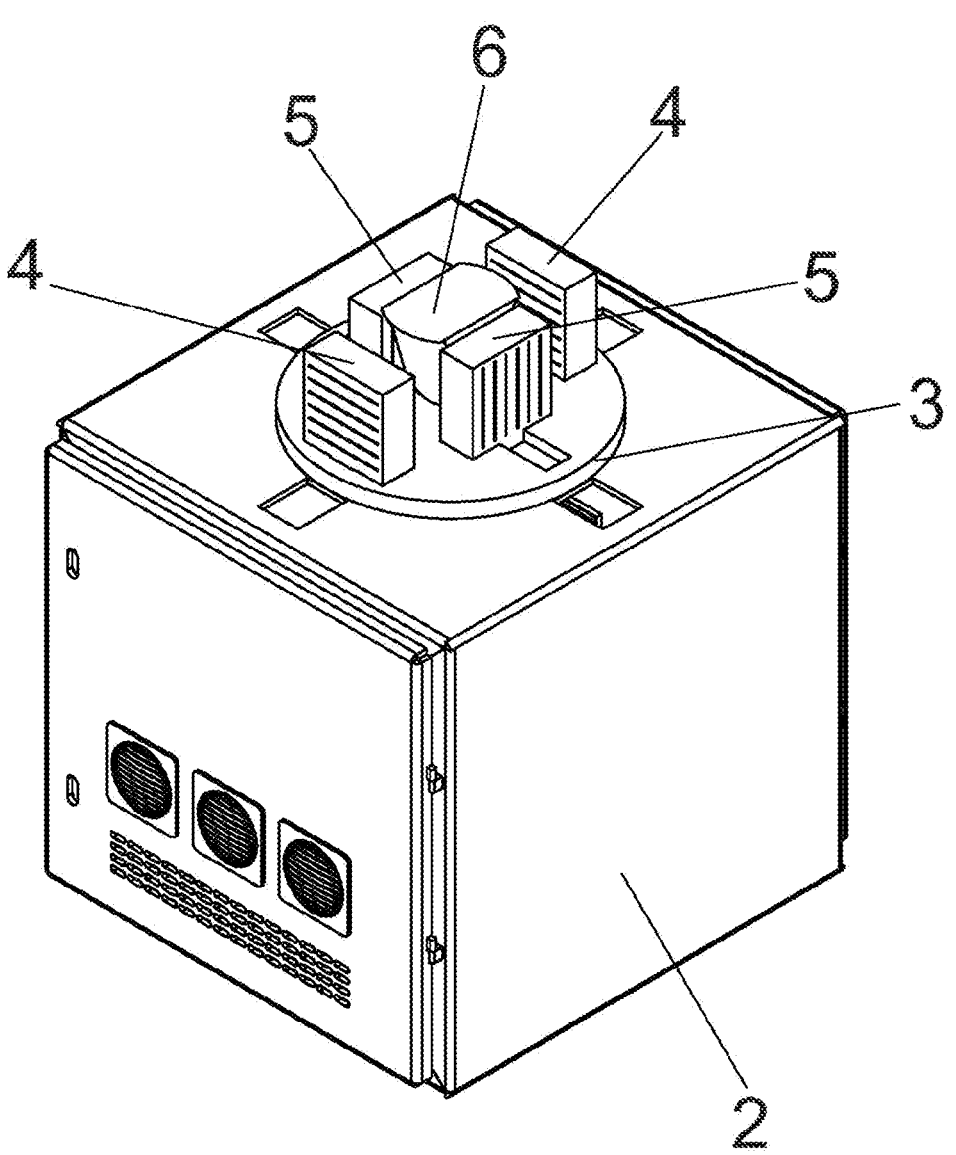
FIG. 8 illustrates the view of a state in which the breast tissue is compressed by the main measurement unit included in the screening system and the measuring operation is performed by means of the vertically polarized antennas.
Figure 9:
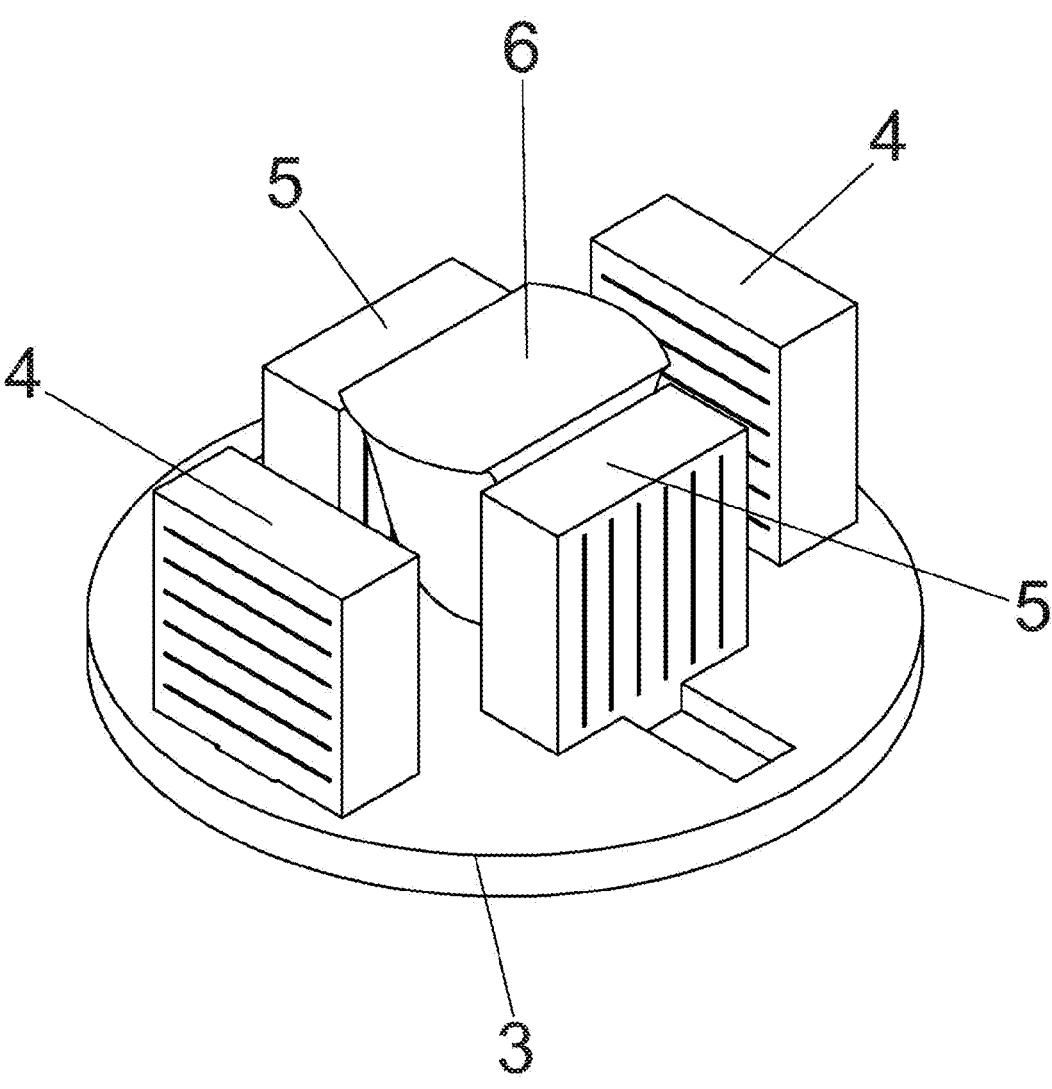
FIG. 9 illustrates the view of a state in which the breast tissue is compressed by the antenna blocks included in the screening system and the measurement operation is performed by means of the vertically polarized antennas.
Figure 10:
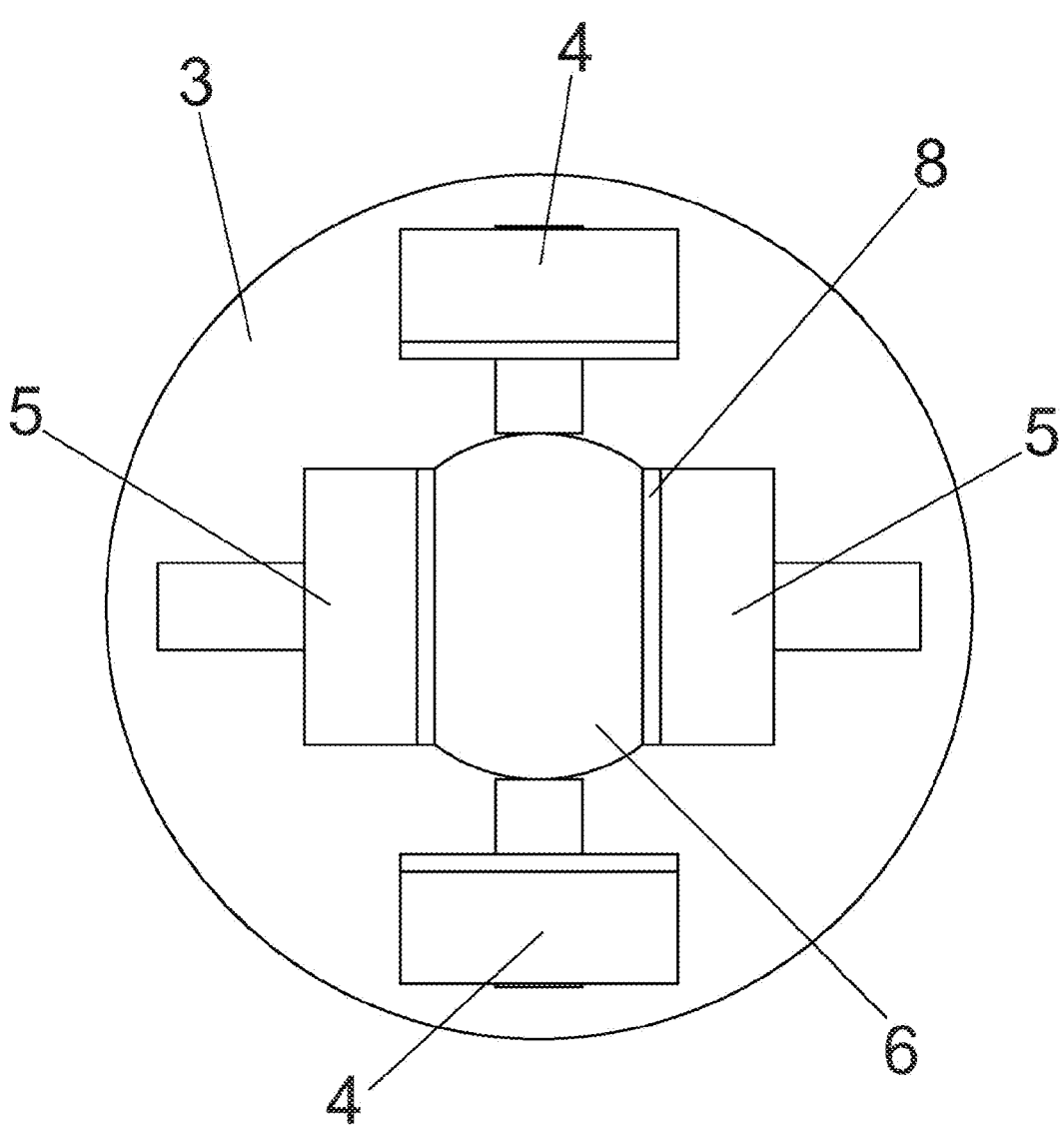
FIG. 10 illustrates the view of a state in which the breast tissue is compressed by the antenna blocks included in the screening system in a case where a matching media is available, and the measurement operation is performed by means of the vertically polarized antennas.
Figure 11:
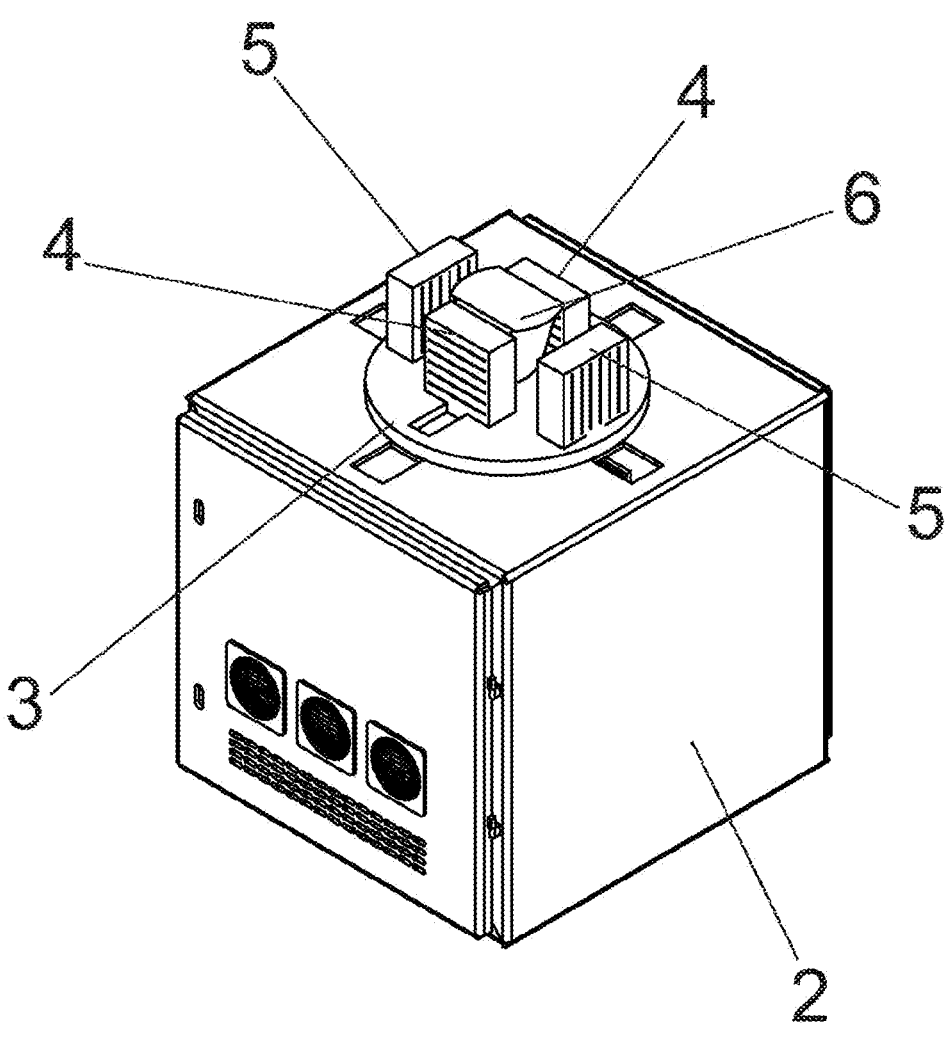
FIG. 11 illustrates the view of a state in which the breast tissue is compressed by the main measurement unit included in the screening system and the measurement operation is performed by means of the horizontally polarized antennas.
Figure 12:
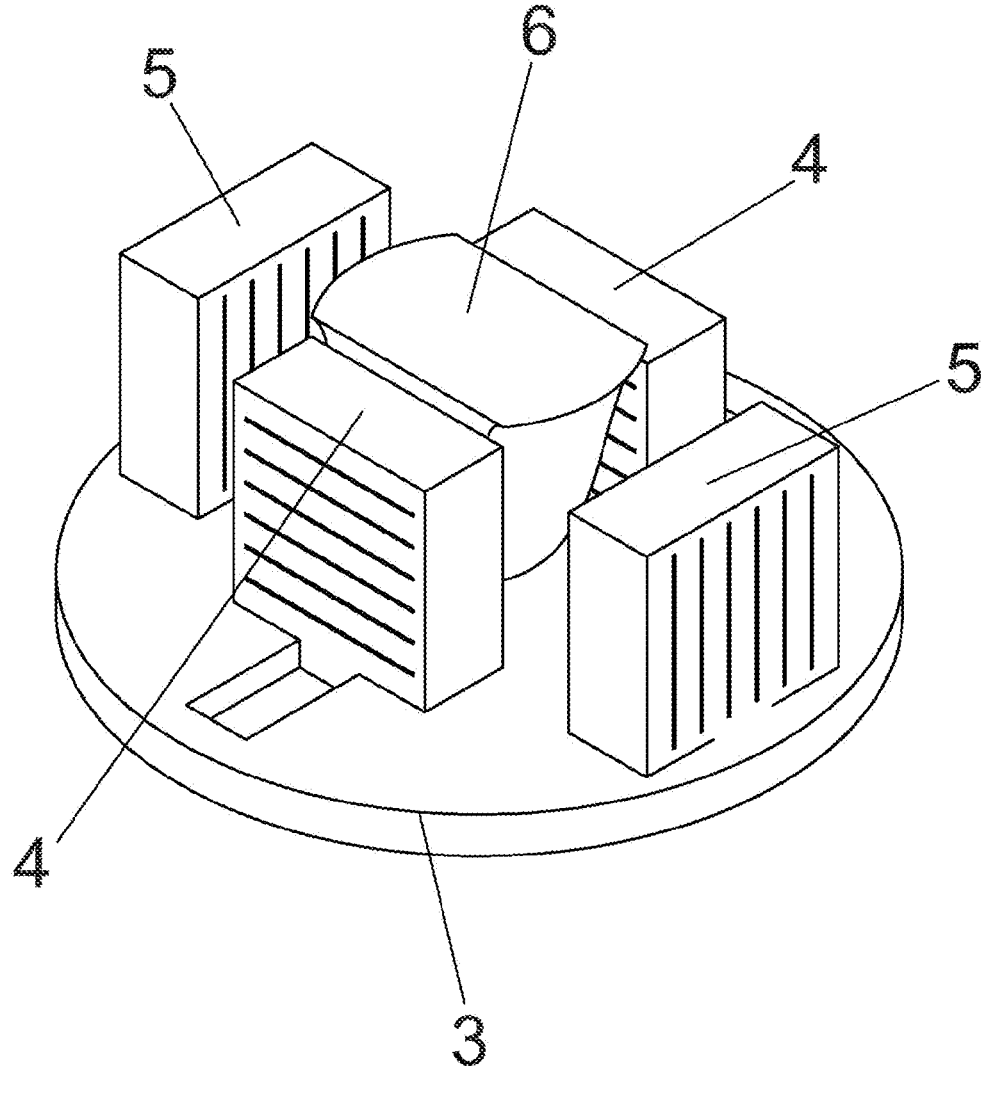
FIG. 12 illustrates the view of a state in which the breast tissue is compressed by the antenna blocks included in the screening system and the measurement operation is performed by means of the horizontally polarized antennas.
Figure 13:
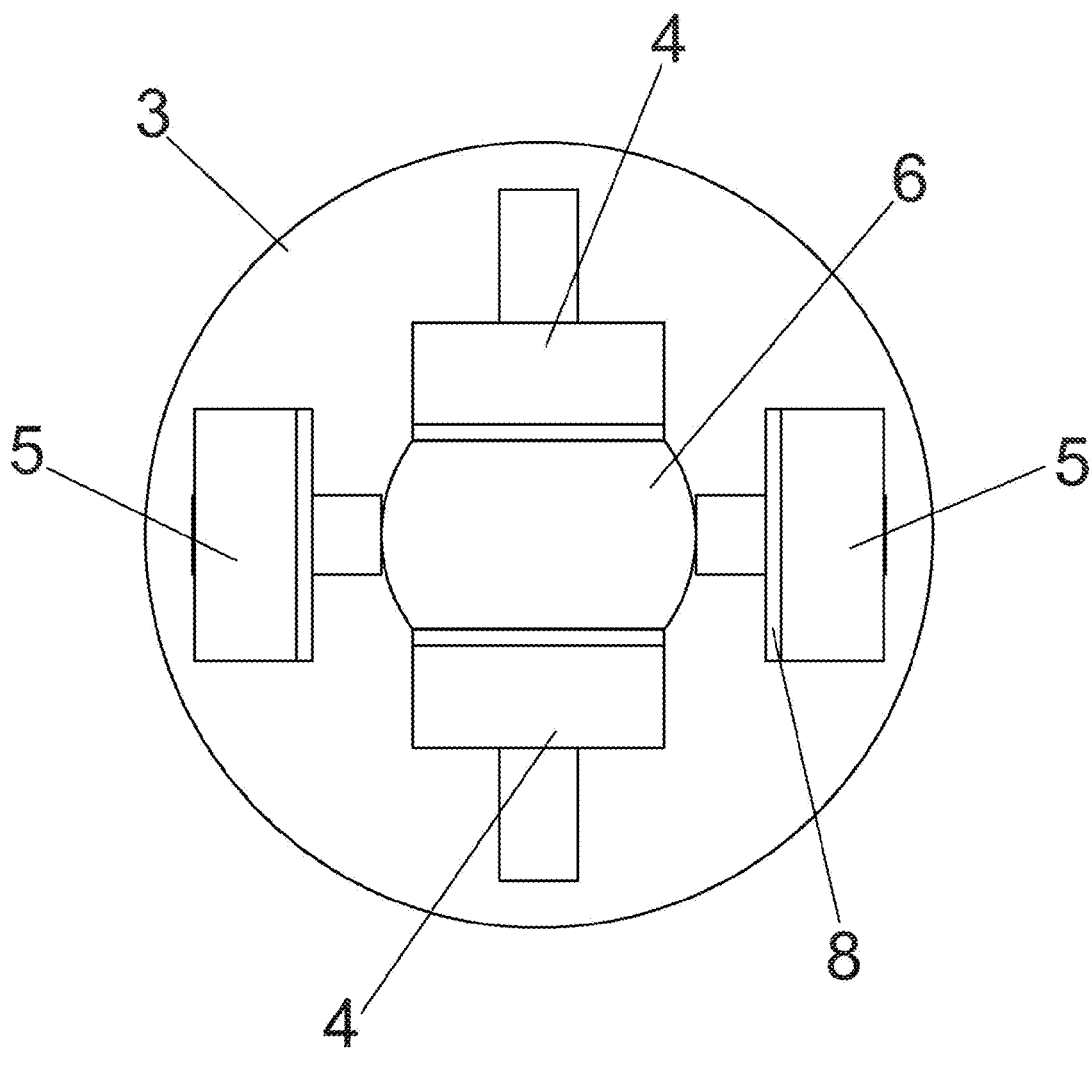
FIG. 13 illustrates the top view of a state in which the breast tissue is compressed by the antenna blocks included in the screening system in a case where a matching media is available, and the measurement operation is performed by means of the horizontally polarized antennas.
Figure 14:
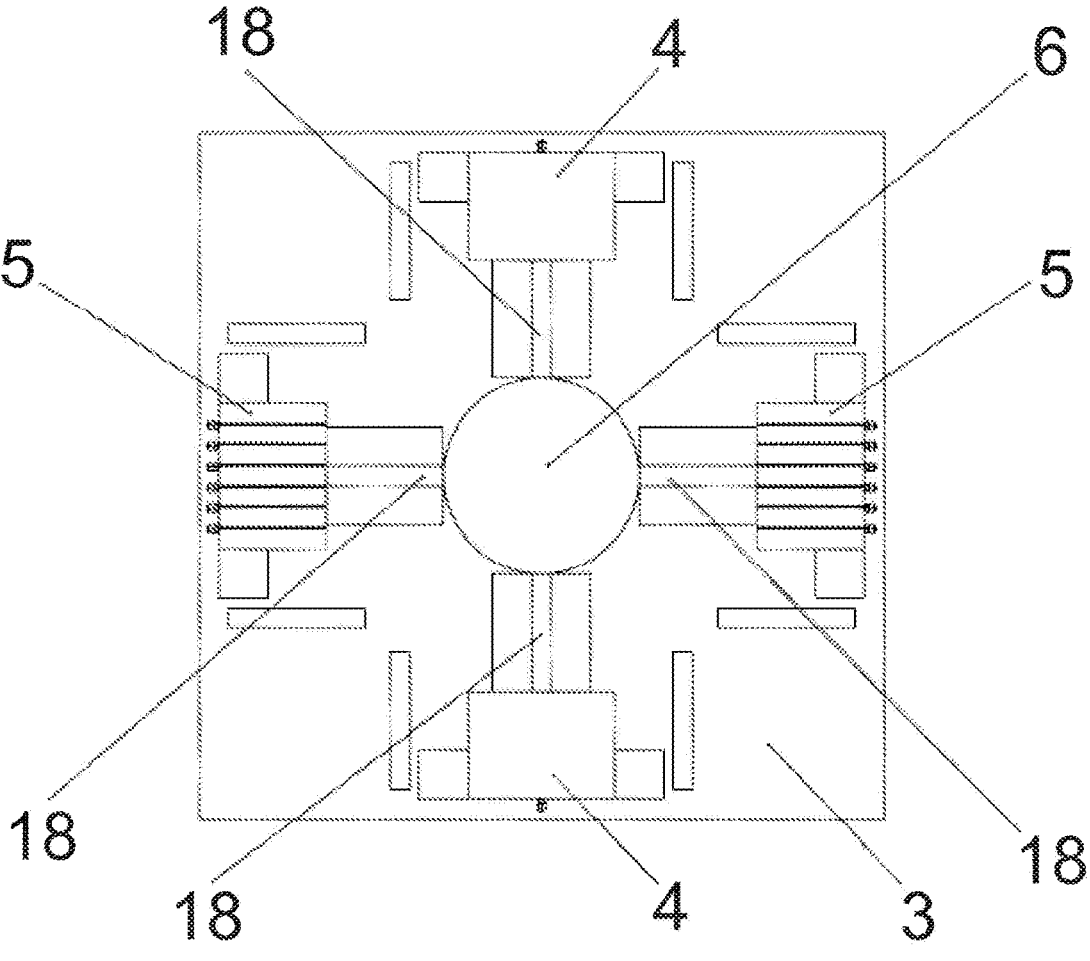
FIG. 14 illustrates the top view of the main measurement unit included in the screening system in an empty state.
Figure 15:
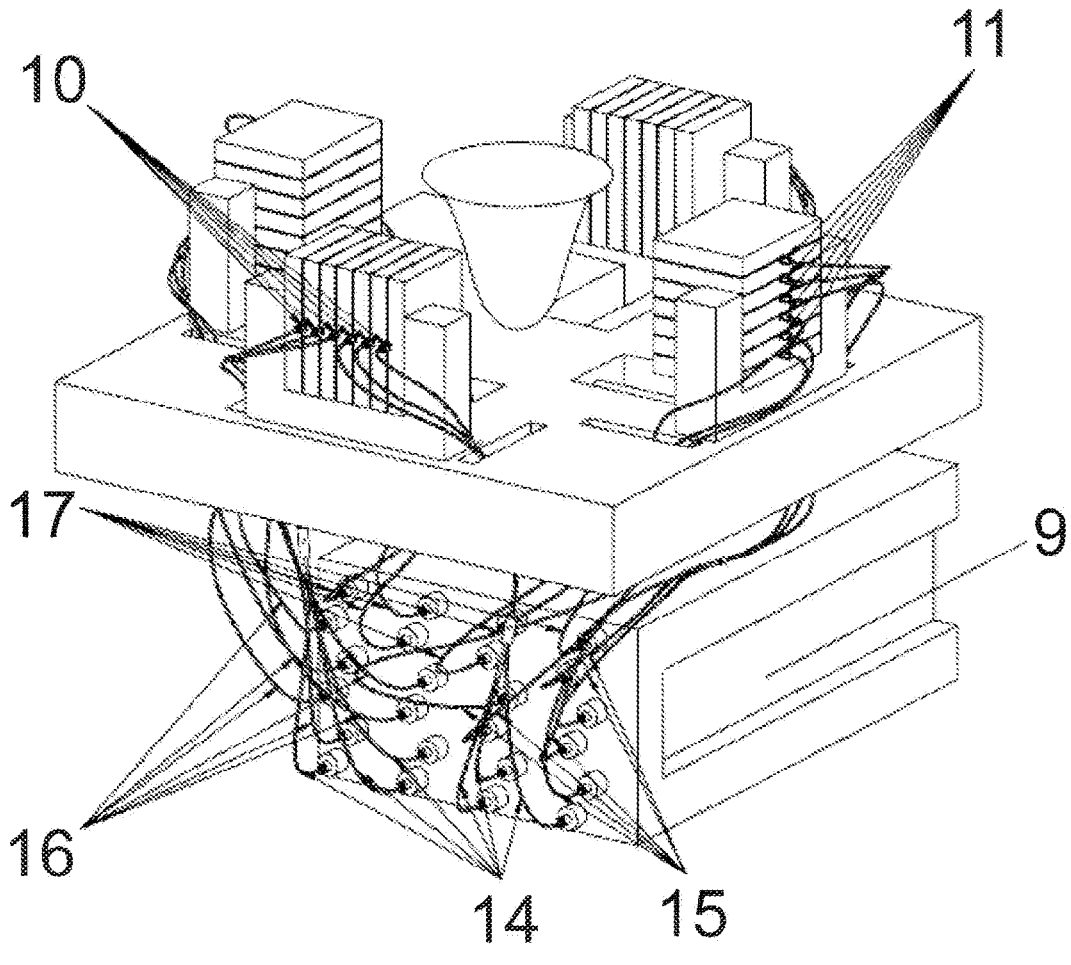
FIG. 15 illustrates the perspective view of RF cable units connecting S-parameter measurement unit, vertically and horizontally polarized antenna inputs/outputs, S-parameter measurement unit inputs/outputs, antenna and S-parameter measurement unit inputs/outputs of the main measurement unit included in the screening system with an empty state.
Figure 16:
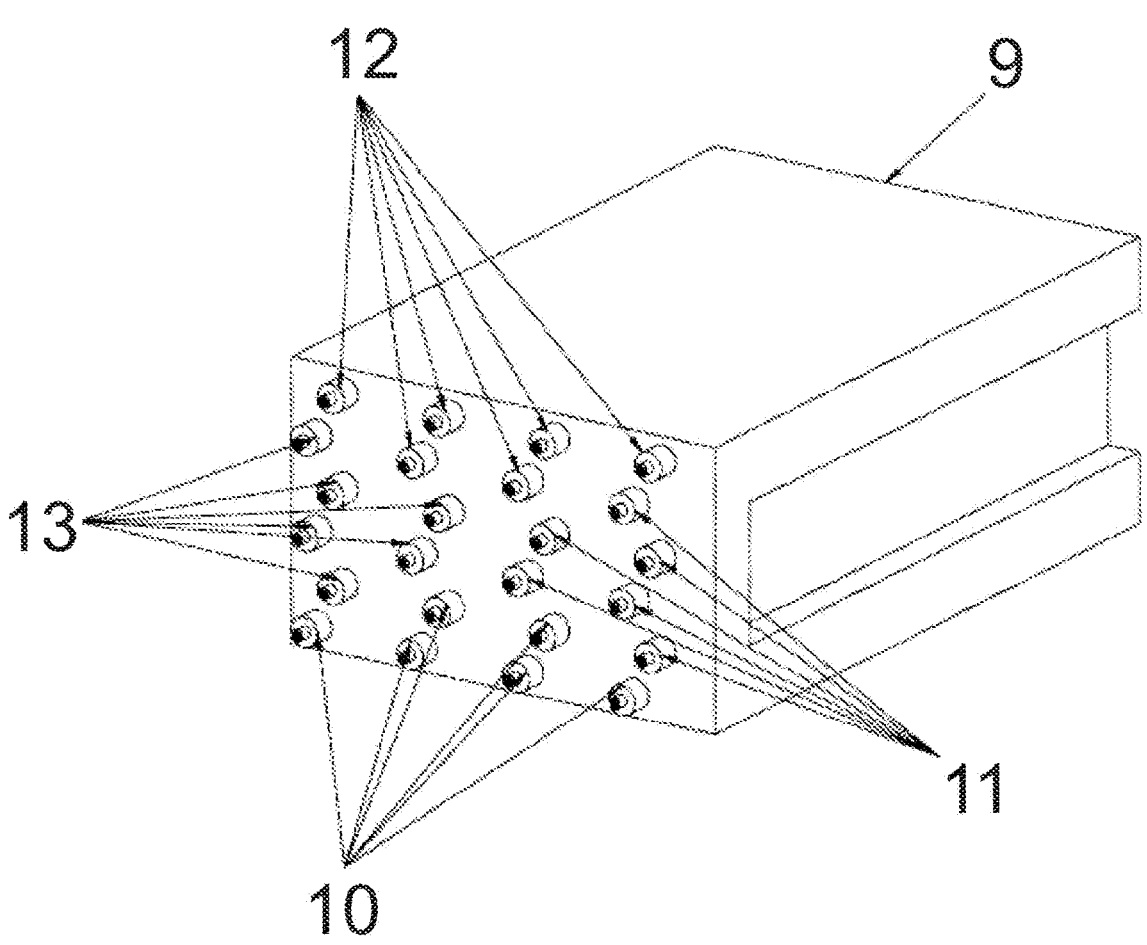
FIG. 16 illustrates the perspective view of the S-parameter measurement unit inputs/outputs included in the main measurement unit of the screening system.
Figure 17:
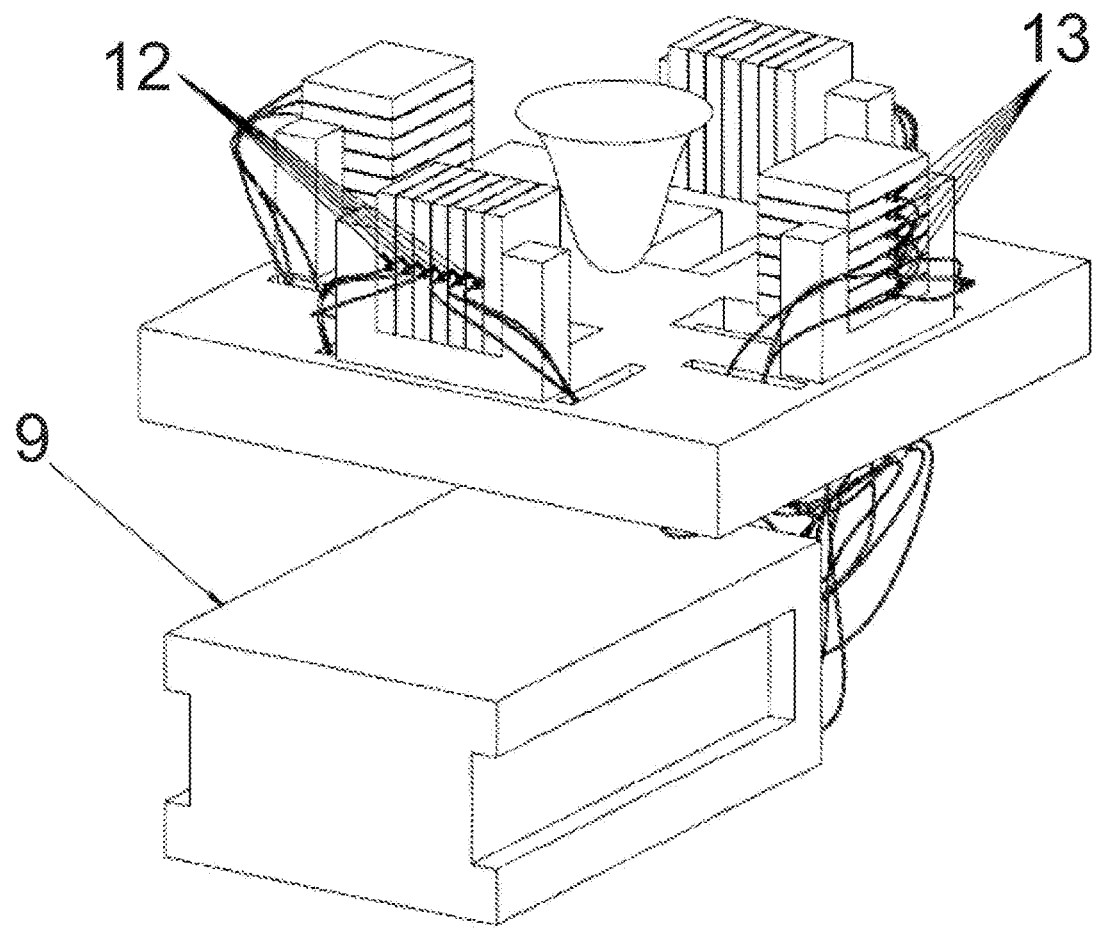
FIG. 17 illustrates the perspective view of the S-parameter measurement unit, vertically and horizontally polarized antenna inputs/outputs of the main measurement unit of the screening system with an empty state.

Components illustrated in figures are individually enumerated and the equivalents of said numbers are provided below.

1. Bed compartment
2. Main measurement unit
3. Turntable mechanism
4. Horizontally polarized antenna block
5. Vertically polarized antenna block
6. Breast tissue
7. Opening
8. Impedance matching media 9. S-Parameter measurement unit
10. Vertically polarized antenna inputs and S-parameter measurement unit outputs corresponding these inputs
11. Horizontally polarized antenna inputs and S-parameter measurement unit outputs corresponding these inputs
12. Vertically polarized antenna inputs and S-parameter measurement unit outputs corresponding these inputs
13. Horizontally polarized antenna inputs and S-parameter measurement unit outputs corresponding these inputs
14. RF cables connecting the vertically polarized antenna inputs and S-parameter measurement unit outputs corresponding these inputs
15. RF cables connecting horizontally polarized antenna inputs and S-parameter measurement unit outputs corresponding these input points
16. RF cables connecting horizontally polarized antenna inputs and S-parameter measurement unit outputs corresponding these input points
17. RF Cables connecting the vertically polarized antenna inputs and S-parameter measurement unit outputs corresponding these inputs
18. Rail system

DETAILED DESCRIPTION OF THE EMBODIMENTS

The breast cancer screening system invention comprises the components of;
  a rectangular shaped bed compartment (1) with an opening (7) located at the top of the bed which allows the breast tissue (6) to be placed and positioned between antenna blocks,
  a main measurement unit (2) that is located inside the bed compartment (1), that allows the saving of S-parameters and using these parameters for microwave image reconstruction and performing S-parameter comparisons and that comprises a computing unit containing a microwave imaging algorithm, deep learning and machine learning algorithms,
  a disk-shaped turntable mechanism (3) that is positioned inside the bed compartment (1), that comprises gaps located thereon, and that allows for collecting data from different horizontal and vertical breast sections through angular movement,
  a horizontally polarized antenna block (4) that is located on the turntable mechanism (3) and on which, horizontally polarized linear-array antennas are located,
  a vertically polarized antenna block (5) that is located on the turntable mechanism (3) and on which, vertically polarized linear-array antennas are located,
  an S-parameter measurement unit (9) that excites microwave signals to antenna located inside the main measurement unit (2) and that allows scattering parameters to be collected,
  a rail system (18) that is positioned on the turntable mechanism (3), and that allows the breast tissue (6) to be compressed via planar (linear) movement of the horizontally polarized antenna block (4) and of the vertically polarized antenna block (5).
The novel screening system enables acquisition of microwave images from various vertical, horizontal and angular sections of the breast tissue (6) since the antennas arranged as a planar (linear) array are capable of performing both angular and planar movements. The system is envisaged to be operated by using frequency domain and inverse scattering based microwave imaging algorithms. These algorithms are divided into two categories: qualitative and quantitative. Qualitative inverse scattering methods attempt to reconstruct the shape of inaccessible targets from scattered fields without making any assumptions on the number of targets or their electrical properties. Quantitative methods aim to retrieve electrical properties of the illuminated targets. As such, the scattering problem can be presented as a minimization of a nonlinear function, or transformed into minimization of a linear function under Born approximation[1] and/or by implementing virtual experiments[2]. Qualitative imaging techniques may be utilized for deciding whether a malignant/cancerous tissue is located or not inside the breast. The appealing feature of their implementation into the areas of breast cancer early screening and diagnosis is their computational efficiency. Fast and robust reconstructions can be achieved via so called indicator function $\chi$ which holds the properties of the domain of interest. In order to mathematically determine the indicator function, assume that the measuring and illuminating antennas are located on the surface $\Gamma$, surrounding scattering object $\Omega$ (cancerous tissue) and the sampling domain D, which in this case would be breast tissue (6), sampled by a grid of points rs (xs, ys). The algorithm consists in solving, for each sampling point rs, the matrix equation, $$[E_s][\chi(r_s)] = g(r_s) \tag{1}$$

In Equation (1), $[E_s]$ is the N×N multistatic response matrix (MRM) whose $i^{th}$ row is the field at the N receivers when $i^{th}$ transmitter is radiating, x is the N-dimensional unknown vector, and $g(r_s)$ stands for the Green's function of the background medium in the sampling point evaluated at receivers. In the considered scenario, MRM is obtained from the measurements, and is defined as difference between measured parameters S1 when the target is present inside the domain D (breast (6) affected by the tumor) and S0 when there is no target inside D (breast (6) is healthy, there is no tumor inside the tissue).

$$E_s = S_1 - S_0 \tag{2}$$

Due to the properties of MRM [3], the problem at hand (1) is ill-conditioned. Thus, in order to obtain a reliable solution, regularization should be considered. Exploiting singular value decomposition (SVD)[3] and Tikhonov regularization [3] a stable solution is explicitly achieved in the following form:

$$\chi(r_s) = \sum_{n=0}^{N} \frac{\lambda_n}{\lambda_n^2 + \alpha^2} \langle g(r_s), u_n \rangle v_n \tag{3}$$

where $\alpha$ denotes the Tikhonov regularization parameter, $\lambda_n$ stands for singular values of MRM, $u_n$ and $v_n$ are left and right singular vectors, respectively, and $\langle \cdot, \cdot \rangle$ stands for scalar product on T. As the $L^2$ norm of regularized solution $\chi(r_s)$ assumes low values when rs belongs to targets and large elsewhere, computing the $L^2$ norm ($\|\chi\|$) on $\Gamma$ gives the geometrical features of the target. It is worth mentioning that main computational effort is the computation of SVD of MRM, and that this task is performed only once, as the kernel of linear system is same for every sampling point.

In the proposed breast cancer screening system invention, breast tissue (6) is inserted into the system through the opening (7) located on the bed compartment (1). After the breast tissue (6) is positioned into the system, it is compressed with the planar movement of the horizontally polarized antenna blocks (4) on the rail system (18) where data collected, by means of the S-parameter measurement unit (9), is used to provide vertical section reconstruction of the breast. This procedure is repeated for vertically polarized antenna blocks (5), where the data collected (S-parameters) are used for horizontal section breast reconstruction. Antenna inputs/outputs (11-13) in the horizontally polarized antenna block (4) are connected to the corresponding inputs/outputs (11-13) of the S-parameter measurement unit (9) using RF cables (15-16). Antenna inputs/outputs (10-12) of the vertically polarized antenna block (5) are connected to the corresponding inputs/outputs (10-12) of the S-parameter measurement unit (9) using RF cables (14-17). After data is collected using both orientations (horizontal and vertical polarization blocks), the position of the vertically polarized antenna block (5) and the horizontally polarized antenna block (4) is changed relative to the breast tissue (6) by the angular movement of the turntable mechanism (3), and data is collected in the same manner using the S-parameter measurement unit (9). Subsequently, the data is processed by the computing unit and sectional microwave images of the breast tissue (6) are generated.

In the proposed system subject of invention, horizontal and vertical antennas are positioned such that they are mutually arranged as horizontally polarized antenna block (4) and vertically polarized antenna block (5) in a planar direction. Additionally, the breast tissue (6) is stationary, and the antennas are made such that they are capable of performing both planar and angular movement. The antennas located on the vertically polarized antenna block (5) are positioned perpendicular to the x-y plane and the antennas located on the horizontally polarized antenna block (4) are positioned parallel to the x-y plane. Thus, the aim is to acquire both horizontal and vertical sectional images of the breast (6).

The proposed system subject of invention, contrary to the microwave systems available in the literature, performs planar screening instead of cylindrical or spherical screening. Using planar screening, mild compression of the breast (6) is enabled, which allows lower attenuation in the penetrating waves. The imaging system will provide angular as well as multi sectional imaging by altering the positions of the scanning blocks as well as the polarization of the antennas used for the scanning. 3D reconstruction is achieved by merging the horizontal and vertical sections thus providing the complete information about the axial and coronal/vertical position of the cancerous tissue. Additionally, multi-angle reconstructions sections may be subjected to a comparison and used for cross validation in order to evaluate the consistency during the scanning.

In the proposed system of invention, horizontally polarized antenna block (4) allows to reconstruct the horizontal cross-section of the breast (6), thus, if present, providing an information about the position of the malignant/cancerous tissue at the transverse plane inside the breast (6).

Vertically polarized antenna block (5) allows to reconstruct the vertical cross-section of the breast (6) thus, if present, providing an information about the position of the malignant/cancerous tissue at the vertical (sagittal/coronal/other) plane inside the breast (6).

Correlating the information acquired from both antenna blocks, namely, horizontally polarized antenna blocks (4) and vertically polarized antenna blocks (5) a 3D image reconstruction of the breast health condition (6), as well as, if present, of the malignant/cancerous tissue inside the breast (6), is, possible.

Horizontally polarized antenna block (4) and vertically polarized antenna block (5) can be rotated angularly by means of the turntable mechanism (3), thereby allowing multi-angle 2D sectional reconstruction of the breast tissues (6). 2D cross-sectional reconstructions may be subjected to cross-validation The system, contrary to the ultrasonography or X-ray mammography, can directly provide information about the level of malignancy of the tumour tissue inside the breast based on the produced images. The selectivity of this system, based on the microwave technology, is anticipated to be higher than ultrasonography or mammography. This feature allows the technique to be presented as a non-invasive breast cancer early screening and diagnosis technology that may be used as a complementary technique to biopsy.

In this context, the present invention is expected to;

Enable, in a manner, homogenization of the heterogeneous structure of breast tissue (6).

Decrease the attenuation level of propagating waves by compressing the breast and through decreasing the amount of tissue layer thickness between the antennas and the breast itself.

Allow multi-angle scanning of the breast and use cross validation to evaluate the consistency of the scans and presence of the malignant/cancerous tissue.

Enable multi 2D reconstructions (horizontal and vertical cross-sections) using antenna blocks with different antenna polarizations. Thus, give the possibility of 3D representation of the breast tissue (6) health condition.

The proposed breast cancer screening system, subject of this invention, is envisaged to significantly improve functional imaging by implementing the aforementioned contributions.

The proposed breast cancer screening system, subject of this invention, is expected to eliminate the problems associated with the attenuation of wave propagation stemming from the tissue heterogeneity and inherently lossy nature of the tissue. Accuracy rates of diagnostics are expected to improve upon the adoption of planar approach in the system.

The system will utilize S-parameters collected via using antennas with both horizontal and vertical polarizations as well as machine learning and deep learning algorithms to provide the information regarding the presence of malignant/cancerous tissue inside the breast (6).

The invention is capable of obtaining a plurality of images from a single measurement operation by using a plurality of microwave imaging algorithms and can establish a diagnosis by analysing these images through machine learning or deep learning.

The measurement operation, which is classified as a non-invasive one, is based on the difference in dielectric properties (permittivity and conductivity) between the breast (6) and the malignant/cancerous tissues.

REFERENCES

[1] W. C. Chew, "Waves and Fields in Inhomogenous_Media". IEEE press New York, 1995.
[2] L. Di Donato, M. T. Bevacqua, L. Crocco, and T. Isernia, "Inverse Scattering Via Virtual Experiments and Contrast Source Regularization," IEEE Trans. Antennas Propag., vol. 63, no. 4, pp. 1669-1677, 2015.

[3] D. Colton and R. Kress, "Inverse Acoustic and Electromagnetic Scatterin Theory". Berlin, Germany: Springer-Verlang, 1992.

What is claimed is:

1. A breast cancer screening system, comprising:

a bed compartment of a rectangular shape, wherein the bed compartment is located inside the breast cancer screening system, and an opening is located on the bed compartment and allows a breast to be positioned, wherein the bed compartment comprises antennas to receive microwave signals for acquiring microwave images from S-parameters and making a comparison of the S-parameters, a disk-shaped turntable mechanism positioned inside the bed compartment, wherein the disk-shaped turntable mechanism comprises gaps located on the disk-shaped turntable mechanism, and the disk-shaped turntable mechanism allows for collecting data from different horizontal and vertical breast cross-sections through an angular motion, a horizontally polarized antenna block located on the disk-shaped turntable mechanism, wherein horizontally polarized linear-array antennas are located on the horizontally polarized antenna block, a vertically polarized antenna block located on the disk-shaped turntable mechanism, wherein vertically polarized linear-array antennas are located on the vertically polarized antenna block, and a rail system positioned on the disk-shaped turntable mechanism, wherein the rail system allows the breast to be compressed via a planar or linear movement of the horizontally polarized antenna block and a planar or linear movement of the vertically polarized antenna block.

2. The breast cancer screening system according to claim 1, further comprising impedance matching media positioned on a front surface of the horizontally polarized antenna block and the vertically polarized antenna block, wherein the impedance matching media comes into contact with the breast.

* * * * *